United States Patent [19]

Waltersdorfer et al.

[11] Patent Number: 5,139,785
[45] Date of Patent: Aug. 18, 1992

[54] PESTICIDES

[75] Inventors: Anna Waltersdorfer, Frankfurt am Main; Manfred Kern, Lörzweiler; Werner Knauf, Eppstein/Taunus; Hans H. Schubert, Frankfurt am Main, all of Fed. Rep. of Germany

[73] Assignee: Hoechst Aktiengesellschaft, Frankfurt am Main, Fed. Rep. of Germany

[21] Appl. No.: 657,285

[22] Filed: Feb. 19, 1991

Related U.S. Application Data

[63] Continuation of Ser. No. 327,738, Mar. 23, 1989, abandoned.

[30] Foreign Application Priority Data

Mar. 26, 1988 [DE] Fed. Rep. of Germany ....... 3810378

[51] Int. Cl.$^5$ ............................................. A01N 33/08
[52] U.S. Cl. ......................................... 424/405; 514/63; 514/431
[58] Field of Search ............... 514/63, 431; 424/405

[56] References Cited

U.S. PATENT DOCUMENTS

| | | | |
|---|---|---|---|
| 3,780,175 | 12/1973 | Barcza | 514/63 |
| 4,663,314 | 5/1987 | Hayase et al. | 514/63 |
| 4,709,068 | 11/1987 | Sieburth | 549/4 |
| 4,769,481 | 9/1988 | Koch et al. | 558/9 |
| 4,775,664 | 10/1988 | Schubert et al. | 514/63 |

FOREIGN PATENT DOCUMENTS

| | | |
|---|---|---|
| 71748/87 | 4/1986 | Australia . |
| 0135894 | 9/1984 | European Pat. Off. . |
| 0243790 | 10/1986 | European Pat. Off. . |
| 0224024 | 4/1987 | European Pat. Off. . |
| 0249015 | 12/1987 | European Pat. Off. . |
| 8807271 | 2/1988 | PCT Int'l Appl. . |

Primary Examiner—Lester L. Lee
Attorney, Agent, or Firm—Curtis, Morris & Safford

[57] ABSTRACT

Pesticides containing at least one compound of the formula I

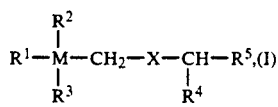

where
M denotes carbon or silicon,
X denotes $CH_2$, O, S, $NR^6$,
$R^1$ denotes $(C_2-C_{18})$alkyl, $(C_5-C_7)$cycloalkyl, $(C_2-C_8)$alkenyl, phenyl, naphthyl, pyridyl, pyrimidyl, pyridazinyl, pyrazinyl, 1,2,4-triazinyl or 1,2,4,5-tetrazinyl, it being possible for all these substituents to be monosubstituted or polysubstituted, $R^2$, $R^3$ independently of one another denote $(C_1-C_3)$alkyl, $(C_2-C_8)$alkenyl or phenyl, or $R^2$ and $R^3$ denote an alkylene chain which—together with the quaternary central atom (M)—form an unsubstituted or fluorine-substituted ring having four to six ring members (where M=Si) or having three to six ring members (where M=C), $R^4$ denotes —H, —CN, —$CCl_3$, —C≡CH, $(C_1-C_4)$alkyl, F,

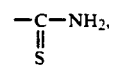

$R^5$ denotes pyridyl, furyl or thienyl, each of which can be substituted, phthalimidyl, di($C_1-C_4$)alkylmaleimidyl, thiophthalimidyl, dihydrophthalimidyl, tetrahydrophthalimidyl or substituted phenyl, or $R^4$ and $R^5$ —together with the carbon atom linking them—form an optionally substituted indanyl, cyclopentenoyl or cyclopentenyl radical, and $R^6$ denotes H, $(C_1-C_3)$alkyl or phenyl, in combination with a compound from the group comprising endosulfan (IX), buprofezin (X), cyromazine (XI), flubenzimine (XIII), flufenoxuron (XIII), deltamethrin (XIIIa), triazophos (XIIIb) and heptenophos (XIIIc), or a compound of the formula XIV

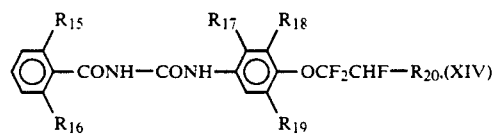

where
$R_{15}$, $R_{16}$, $R_{17}$ and $R_{18}$ independently of one another denote hydrogen or halogen,
$R_{19}$ denotes $CH_3$, $CF_3$ or halogen and
$R_{20}$ denotes $(C_1-C_3)$haloalkyl, or a compound of the formula XV

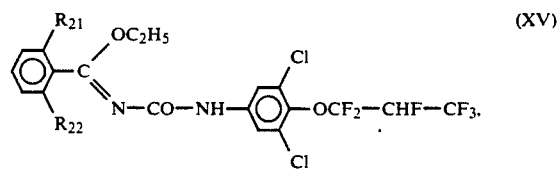

where $R_{21}$ and $R_{22}$ independently of one another denote H or halogen, show advantageous synergistic effects.

24 Claims, No Drawings

PESTICIDES

This application is a continuation of application Ser. No. 07/327,738, filed Mar. 23, 1989, now abandoned.

EP-A 0,249,015 and 0,224,024 disclose insecticidal and acaricidal agents which contain a compound of the formula I

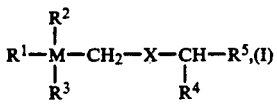

where
M denotes carbon or silicon,
X denotes $CH_2$, O, S, $NR^6$,
$R^1$ denotes $(C_2-C_{18})$alkyl, $(C_5-C_7)$cycloalkyl, $(C_2-C_8)$alkenyl, phenyl, naphthyl, pyridyl, pyrimidyl, pyridazinyl, pyrazinyl, 1,2,4-triazinyl or 1,2,4,5-tetrazinyl, it being possible for all these substituents to be monosubstituted or polysubstituted,
$R^2$, $R^3$ independently of one another denote $(C_1-C_3)$alkyl, $(C_2-C_8)$alkenyl or phenyl, or $R^2$ and $R^3$ denote an alkylene chain which—together with the quaternary central atom (M)—form an unsubstituted or fluorinesubstituted ring having four to six ring members (where M = Si) or having three to six ring members (where M = C),
$R^4$ denotes —H, —CN, —$CCl_3$, —C≡CH, $(C_1-C_4)$alkyl, F,

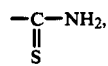

$R^5$ denotes pyridyl, furyl or thienyl, each of which can be substituted, phthalimidyl, di($C_1-C_4$)alkylmaleimidyl, thiophthalimidyl, dihydrophthalimidyl, tetrahydrophthalimidyl or substituted phenyl, or $R^4$ and $R^5$ —together with the carbon atom linking them—form an optionally substituted indanyl, cyclopentenoyl or cyclopentenyl radical, and
$R^6$ denotes H, $(C_1-C_3)$alkyl or phenyl.

These patents also describe processes for the preparation of compounds of the formula I. Preferred meanings in the compounds of the formula I are:
$X = CH_2$ or oxygen,
$R^1$ = a group of the general formulae II to VIII

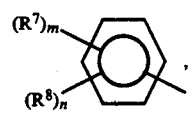

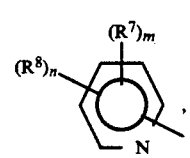

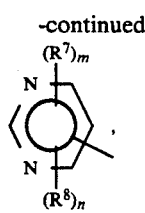

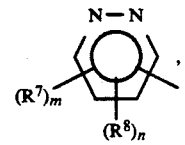

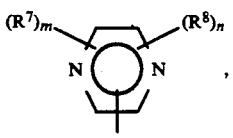

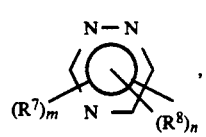

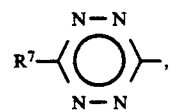

where
$R^7$ and $R^8$ independently of one another denote a radical linked to a carbon atom, from the group comprising H, $(C_1-C_4)$alkyl, tri$(C_1-C_4)$alkylsilyl, halogen, nitro, cyano, $(C_2-C_6)$alkenyl, $(C_2-C_6)$alkynyl, amino, $(C_3-C_7)$cycloalkyl, phenyl, phenoxy, $(C_1-C_5)$alkoxy, $(C_2-C_4)$alkenyloxy, $(C_2-C_4)$alkynyloxy, hydroxycarbonyl, $(C_1-C_5)$alkylthio, $(C_3-C_7)$cycloalkyloxy, $(C_1-C_6)$alkylcarbonyl, $(C_1-C_4)$alkoxycarbonyl, $(C_2-C_4)$alkenyloxycarbonyl, $(C_3-C_5)$alkynyloxycarbonyl, $(C_1-C_4)$haloalkyl $(C_1-C_4)$alkoxy$(C_1-C_4)$alkyl, $(C_1-C_3)$haloalkoxy, $(C_1-C_3)$haloalkylthio, halo$(C_1-C_4)$alkoxy$(C_1-C_4)$alkyl, $(C_1-C_4)$alkylthio$(C_1-C_4)$alkyl, $(C_1-C_4)$alkoxy$(C_1-C_4)$alkoxy, halo$(C_1-C_4)$alkoxy$(C_1-C_4)$alkoxy,$(C_2-C_4)$alkenyloxy$(C_1-C_4)$alkoxy, halo$(C_2-C_4)$alkenyloxy, $(C_1-C_4)$alkoxy$(C_1-C_4)$alkylthio, $(C_1-C_4)$alkylthio$(C_1-C_4)$alkoxy,$(C_1-C_4)$alkylthio$(C_1-C_4)$alkylthio, halo$(C_1-C_4)$alkoxycarbonyl, halo$(C_2-C_4)$alkenyloxycarbonyl or di$(C_1-C_6$alkyl)amino, or two radicals $R^7$ or $R^8$, when they are in the ortho position to each other, together denote a methylenedioxy, ethylenedioxy or $(C_3-C_5)$alkylene radical, and m and n can assume the values 0, 1 or 2. In a particularly preferred version, $R^7$ and $R^8$ denote hydrogen, halogen, $(C_1-C_4)$alkyl, $(C_2-C_6)$alkenyl, $(C_3-C_7)$cycloalkyl, $(C_1-C_5)$alkoxy, $(C_2-C_4)$alkenyloxy, $(C_1-C_4)$alkylthio, $(C_1-C_4)$haloalkyl or $(C_1-C_3)$haloalkoxy, or 2 radicals $R^7$ or $R^8$ together denote methylenedioxy, $R^7$ and $R^8$ being orientated in particular in the 3- or 4-position of the aromatic ring of six. Other preferred compounds are those in which the total of m and n is 1 or 2.

$R^2$ and $R^3$ preferably denote a $(C_1-C_3)$alkyl radical, such as methyl, ethyl, isopropyl and n-propyl, or together with the carbon atom linking them preferably denote an unsubstituted or monofluorinated or difluorinated cyclopropyl ring where M=C.

$R^4$ preferably denotes hydrogen, fluorine, cyano or $(C_1-C_4)$alkyl, particularly preferably hydrogen.

$R^5$ as substituted phenyl preferably represents a phenyl radical of the formula (A)

 (A)

where $R^9$ substituents independently of one another denote H, halogen, $(C_1-C_4)$alkyl, $(C_1-C_4)$alkoxy, $(C_1-C_4)$haloalkyl, phenyl or n-pyrrolyl or a radical of the formula (B)

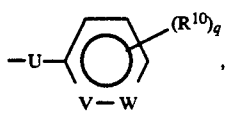 (B)

where the $R^{10}$ substituents independently of one another denote H, halogen, $(C_1-C_4)$alkyl, $(C_1-C_4)$alkoxy or $(C_1-C_4)$haloalkyl; U denotes —$CH_2$—, C=O, —O— or —S—, preferably —O—; V and W denote CH or N where W must denote CH if V=N and vice versa, p denotes an integer from 1 to 5, in particular 1, 2 or, in the event that $R^9$=fluorine, denotes 5, and in the event that $R^9$ corresponds to the group (B), denotes in particular 1 or 2, and q denotes 1 or 2. Particularly important radicals of those which denote $R^5$ are radicals of the formula (A) where $R^9$ denotes H or 4-fluorine and additionally denotes a radical of the formula (B) which is orientated relative to (A) in the 3-position of the phenyl radical.

Optionally substituted pyridyl as $R^5$ in particular denotes a monosubstituted or disubstituted pyridyl group of the general formula (C)

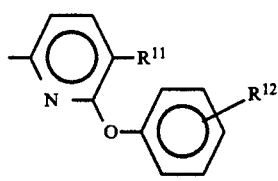 (C)

where $R^{11}$ denotes halogen, in particular fluorine, or H and $R^{12}$ denote hydrogen, halogen with the exception of iodine, $(C_1-C_4)$alkyl, $(C_1-C_4)$alkoxy or $(C_1-C_4)$haloalkyl.

Optionally substituted thienyl as $R^5$ or furyl as $R^5$ in particular represents a heterocycle of the general formula (D),

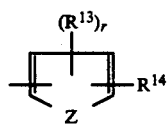 (D)

where Z denotes O or S,
$R^{13}$ denotes H, halogen, $(C_1-C_4)$alkyl, $(C_1-C_4)$alkoxy,
$(C_1-C_4)$haloalkyl, CN or $NO_2$,
$R^{14}$ denotes optionally substituted benzyl, propargyl, allyl or phenoxy and
r denotes 1 or 2.

Compounds where $R^5$ represents substituted phenyl radicals are particularly important in the context of this invention.

Of these, the compound of the formula Ia, in particular, must be singled out

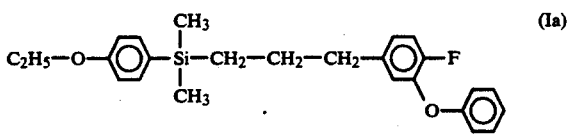 (Ia)

(4-ethoxyphenyl)-(dimethyl)-[3-(4-fluoro-3-phenoxyphenyl)-propyl]-silane

The preparation of this compound is described in EP-A 0,224,024.

Novel combinations of compounds of the formula I with other selected insecticides or acaricides have now been found, which surprisingly shows synergistic effects.

The present invention thus relates to pesticides which contain at least one compound of the formula I in combination with a compound from the group comprising endosulfan (IX), buprofezin (X), cyromazine (XI), flubenzimine (XII), flufenoxuron (XIII), deltamethrin (XIIIa), triazophos (XIIIb) and heptenophos (XIIIc), or a compound of the formula XIV

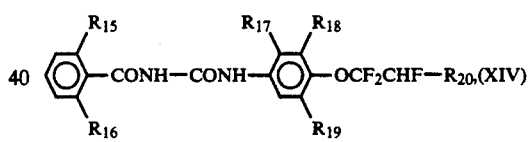 (XIV)

where
$R_{15}$, $R_{16}$, $R_{17}$ and $R_{18}$ independently of one another denote hydrogen or halogen,
$R_{19}$ denotes $CH_3$, $CF_3$ or halogen and
$R_{20}$ denotes $(C_1-C_3)$haloalkyl, or a compound of the formula XV

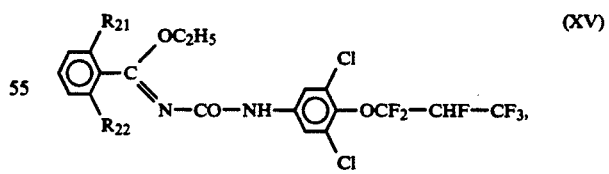 (XV)

where $R_{21}$ and $R_{22}$ independently of one another denote H or halogen.

In the compounds of the formulae XIV and XV, halogen preferably denotes fluorine or chlorine. The radical $R_{20}$ in formula XIV preferably denotes $CF_3$.

From amongst the compounds of the formula XV, the compound of the formula XVa is particularly preferred

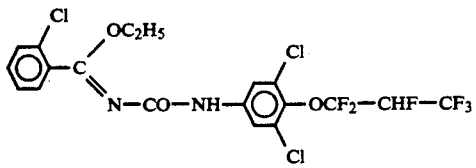

(XVa)

(ethyl N-[N-(3,5-dichloro-4-(1,1,2,3,3,3-hexafluoropropoxy)phenyl)carbamoyl]-2-chloro-benzocarboximidate)

The compound flufenoxuron (XIII) has the formula

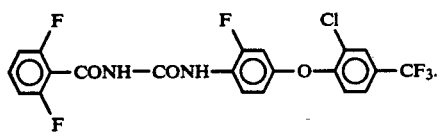

(XIII)

The abovementioned active substances of the formulae IX-XII and XIIIa-XIIIc, for which the common names were indicated, are described in CH. R. Worthing, S. B. Walker, The Pesticide Manual, 8th ed., British Crop Protection Council (1987).

The compounds of the formula XIV and their preparation are described in EP-A 0,243,790, and those of the formula XV in EP-A 0,135,894.

The compound XIII (flufenoxuron) is described in Anderson, H. et al. Proceedings Vol. 1, p. 89–96, British Crop Prot. Conf. (1986).

From experience it is known that the compounds of the formula I can also be combined with two or more of the active substances mentioned.

The insecticidal and acaricidal efficiency of the active substance combination according to the invention is markedly higher than could be expected from the actions of the individual components. By using these combinations, it is therefore possible to reduce the application rates of the individual components. Thus, their use provides economical and ecological advantages.

The agents according to the invention are well tolerated by plants, have a favorable toxicity towards warm-blooded animals, and are suitable for controlling animal pests, in particular insects, arachnids and nematodes, particularly preferably for controlling insects and acarids, and their development stages, which occur in agriculture, in forests, in the protection of stored goods and materials and in the hygiene field. They are active against normally-sensitive and resistant species and against all, or individual, developmental stages. The abovementioned pests include:

From the order of the Isopoda, for example, Oniscus asellus, Armadillidium vulgare and Porcellio scaber.
From the order of the Diplopoda, for example, Blaniulus guttulatus.
From the order of the Chilopoda, for example, Geophilus carpophagus and Scutigera spec.
From the order of the Symphyla, for example, Scutigerella immaculata.
From the order of the Thysanura, for example, Lepisma saccharina.
From the order of the Collembola, for example, Onychiurus armatus.
From the order of the Orthoptera, for example, Blatta orientalis, Periplaneta americana, Leucophaea maderae, Blattella germanica, Acheta domesticus, Gryllotalpa spp., Locusta migratoria migratorioides, Melanoplus differentialis and Schistocerca gregaria.
From the order of the Dermaptera, for example, Forficula auricularia.
From the order of the Isoptera, for example, Reticulitermes spp..
From the order of the Anoplura, for example, Phylloxera vastatrix, Pemphigus spp., Pediculus humanus corporis, Haematopinus spp. and Linognathus spp.
From the order of the Mallophaga, for example, Trichodectes spp. and Damalinea spp.
From the order of the Thysanoptera, for example, Hercinothrips femoralis and Thrips tabaci.
From the order of the Heteroptera, for example, Eurygaster spp., Dysdercus intermedius, Piesma quadrata, Cimex lectularius, Rhodnius prolixus and Triatoma spp.
From the order of the Homoptera, for example, Aleurodes brassicae, Bemisia tabaci, Trialeurodes vaporariorum, Aphis gossypii, Brevicoryne brassicae, Cryptomyzus ribis, Doralis fabae, Doralis pompi, Eriosoma lanigerum, Hyalopterus arundinis, Macrosiphum avenae, Myzus spp., Phorodon humuli, Rhopalosiphum padi, Empoasca spp., Euscelis bilobatus, Nephotettix cincticeps, Lecanium corni, Saissetia oleae, Laodelphax striatellus, Nilaparvata lugens, Aonidiella aurantii, Aspidiotus hederae, Pseudococcus spp. and Psylla spp.
From the order of the Lepidoptera, for example, Pectinophora gossypiella, Bupalus piniarius, Cheimatobia brumata, Lithocolletis blancardella, Hyponomeuta padella, Plutella maculipennis, Malacosoma neustria, Euproctis chrysorrhoea, Lymantria spp., Bucculatrix thurberiella, Phyllocnistis citrella, Agrotis spp., Euxoa spp., Feltia spp., Earias insulana, Heliothis spp., Laphygma exigua, Mamestra brassicae, Panolis flammea, Prodenia litura, Spodoptera spp., Trichoplusia ni, Carpocapsa pomonella, Pieris spp., Chilo spp., Pyrausta nubilalis, Ephestia kuehniella, Galleria mellonella, Tineola bisselliella, Tinea pellionella, Hofmannophila pseudospretella, Cacoecia podana, Capua reticulana, Choristoneura fumiferana, Clysia ambiguella, Homona magnanima and Tortrix viridana.
From the order of the Coleoptera, for example, Anobium punctatum, Rhizopertha dominica, Acanthoscelides obtectus, Hylotrupes bajulus, Agelastica alni, Leptinotarsa decemlineata, Phaedon cochleariae, Diabrotica spp., Psylliodes chrysocephala, Epilachna varivestis, Atomaria spp., Oryzaephilus surinamensis, Anthonomus spp., Sitophilus spp., Otiorrhynchus sulcatus, Cosmopolites sordidus, Ceuthorrhynchus assimilis, Hypera postica, Dermestes spp., Trogoderma spp., Anthrenus spp., Attagenus spp., Lyctus spp., Meligethes aeneus, Ptinus spp., Niptus hololeucus, Gibbium psylloides, Tribolium spp., Tenebrio molitor, Agriotes spp., Conoderus spp., Melolontha melolontha, Amphimallon solstitialis and Costelytra zealandica.
From the order of the Hymenoptera, for example, Diprion spp., Hoplocampa spp., Lasius spp., Monomorium pharaonis and Vespa spp.
From the order of the Diptera, for example, Aedes spp., Anopheles spp., Culex spp., Drosophila melanogaster, Musca spp., Pannia spp., Calliphora erythrocephala, Lucilia spp., Chrysomyia spp., Cuterebra spp., Gastrophilus spp., Hyppobosca spp., Stomoxys spp., Oestrus spp., Hypoderma spp., Tabanus spp., Tannia spp., Bibio hortulanus, Oscinella frit, Phorbia spp., Pegomyia hyoscyami, Ceratitis capitata, Dacus oleae and Tipula paludosa.

From the order of the Siphonaptera, for example, Xenopsylla cheopis and Ceratophyllus spp,.

From the order of the Arachnida, for example, Scorpio maurus and Latrodectus mactans.

From the order of the Acarina, for example, Acarus siro, Argas spp., Ornithodoros spp., Dermanyssus gallinae, Eriophyes ribis, Phyllocoptruta oleivora, Boophilus spp., Rhipicephalus spp., Amblyomma spp., Hyalomma spp., Ixodes spp., Psoroptes spp., Chorioptes spp., Sarcoptes spp., Tarsonemus spp., Bryobia praetiosa, Panonychus spp. and Tetranychus spp.

The active substance combinations according to the invention are particularly suitable for controlling Heliothis spp., Anthonomus spp. and Trichoplusia spp. and other chewing or sucking insects or spider mites (white fly, Lepidoptera lavae) on cotton, and pests in fruit growing and butterflies in vegetable and wine growing.

The agents according to the invention generally contain to 99% by weight of active substances.

They can be formulated in different ways, as required by the biological and/or chemical-physical parameters. Suitable formulation possibilities are therefore the following: wettable powders (WP), emulsifiable concentrates (EC), aqueous solutions (SC), emulsions, sprayable solutions, oil- or water-based dispersions (SC), suspoemulsions (SC), dusting agents (DP), seed treatment agents, granules in the form of micro granules, granules produced by spraying, coated granules and absorption granules, water-dispersible granules (WG), ULV formulations, microcapsules, waxes or baits.

These individual formulation types are known in principle and are described, for example, in Winnacker-Küchler, "Chemische Technologie" [Chemical Technology], volume 7, C. Hauser Verlag Munich, 4th Ed. 1986; van Falkenberg, "Pesticides Formulations", Marcel Dekker N.Y., 2nd Ed. 1972-73; K. Martens, "Spray Drying Handbook", 3rd Ed. 1979, G. Goodwin Ltd. London.

The formulation auxiliaries required, such as inert materials, surfactants, solvents and other additives are likewise known and are described, for example, in: Watkins, "Handbook of Insecticide Dust Diluents and Carriers", 2nd Ed., Darland Books, Caldwell N.J.; H.v.Olphen, "Introduction to Clay Colloid Chemistry", 2nd Ed., J. Wiley & Sons, N.Y.; Marschen, "Solvents Guide", 2nd Ed., Interscience, N.Y. 1950; McCutcheon,s "Detergents and Emulsifiers Annual", MC Publ. Corp., Ridgewood N.J.; Sisley and Wood, "Encylopedia of Surface Active Agents", Chem. Publ. Co. Inc., N.Y. 1964; Schönfeldt, "Grenzflächenaktive Äthylenoxidaddukte [Boundary-layer active ethylene oxide adducts]", Wiss. Verlagsgesell., Stuttgart 1976; Winnacker-Küchler, "Chemische Technologie [Chemical Technology]", Volume 7, C. Hauser Verlag Munich, 4th Ed. 1986.

On the basis of these formulations, it is also possible to prepare combinations with other pesticidally active substances, fertilizers and/or growth regulators, for example in the form of a ready mix or as a tank-mix. Wettable powders are preparations which are uniformly dispersible in water and which contain, in addition to a diluent or inert substance, wetting agents, for example polyoxyethylated alkylphenols, polyoxyethylated fatty alcohols, alkylsulfonates or alkylphenolsulfonates and dispersing agents, for example sodium ligninsulfonates, sodium 2,2'-dinaphthylmethane-6,6'-disulfonate, sodium dibutylnaphthalenesulfonates or sodium oleylmethyltaurinate. Emulsifiable concentrates were prepared by dissolving the active substance in an organic solvent, for example butanol, cyclohexanone, dimethylformamide, xylene or alternatively higher-boiling aromatics or hydrocarbons with the addition of one or more emulsifiers. Examples of emulsifiers which can be used are: calcium salts of alkylarylsulfonic acids, such as calcium dodecylbenzenesulfonate, or non-ionic emulsifiers, such as fatty acid polyglycol esters, alkylaryl polyglycol ethers, fatty alcohol polyglycol ethers, propylene oxide/ethylene oxide condensation products, alkyl polyethers, sorbitan fatty acid esters, polyoxyethylene sorbitan fatty acid esters or polyoxyethylene sorbitol ester.

Dusting agents are obtained by grinding the active substance with finely divided solid substances, for example talc, natural clays such as kaolin, bentonite, pyrophillite or diatomaceous earth. Granules can be prepared either by spraying the active substance onto adsorptive inert material in the form of granules or by applying active substance concentrates by means of adhesives, for example polyvinyl alcohol, sodium polyacrylate or alternatively mineral oils, onto the surface of carriers, such as sand, kaolinites or of inert material in the form of granules. Granules can also be prepared from suitable active substances in the manner which is customary for fertilizer granules - if desired in a mixture with fertilizers.

In wettable powders, the active substance concentration is, for example, approximately 10 to 90% by weight, the remainder to 100% by weight consists of customary formulation constituents. In the case of emulsifiable concentrates, the active substance concentration can be approximately 5 to 80% by weight. Formulations in the form of dusts usually contain 5 to 20% by weight of active substance, sprayable solutions approximately 2 to 20% by weight. In the case of granules, the active substance content partly depends on if the active compound is present in the liquid or solid state and which granulation auxiliaries, fillers etc. are used.

Besides, the active substance formulations mentioned may contain the adhesives, wetting agents, dispersing agents, emulsifiers, penetrants, solvents, fillers or carriers which are customary in each case.

For use, the concentrates which are present in the commercially available form may be diluted in the customary manner, for example, in the case of wettable powders, emulsifiable concentrates, dispersions and in some cases also in the case of microgranules, by means of water. Preparations in the form of dusts and granules and sprayable solutions are usually not diluted further with inert substances prior to use.

In the agents according to the invention, the weight ratio of the compound of the formula I to the combination partner varies in the range between 20:1 and 1:20, depending on the combination partner to be used. The application concentrations of the combinations can likewise vary depending on the combination partner to be used, namely between 5 g and 3000 g of active substance/ha, in particular between 20 g and 1000 g of active substance/ha.

The examples below serve to illustrate the invention.

A. Formulation examples a) A dusting agent is obtained by mixing 10 parts by weight of active substance and 90 parts by weight of talc as inert substance, and comminuting the mixture in a hand mill.

b) A water-dispersible, wettable powder is obtained by mixing 25 parts by weight of active substance, 65 parts by weight of kaolin-containing quartz as inert substance, 10 parts by weight of potassium ligninsulfonate and 1 part by weight of sodium oleoyl methyl taurinate as wetting and dispersing agent, and grinding the mixture in a pin-disk mill.

c) A dispersion concentrate which is readily dispersible in water is prepared by mixing 40 parts by weight of active substance with 7 parts by weight of a sulfosuccinic acid monoester, 2 parts by weight of a sodium salt of ligninsulfonic acid and 51 parts by weight of water, and grinding the mixture in a ball mill to a fineness of below 5 micron.

d) An emulsifiable concentrate may be prepared from 15 parts by weight of active substance, 75 parts by weight of cyclohexanone as solvent and 10 parts by weight of oxyethylated nonylphenol (10 EO) as emulsifier.

e) Granules can be prepared from 2 to 15 parts by weight of active substance and an inert granule carrier material, such as attapulgite, pumice granules and/or quartz sand. A suspension of the wettable powders from example b) having a solids content of 30% is expediently used, and this suspension is sprayed onto the surface of attapulgite granules, and the granules are dried and mixed intimately. In this process, the proportion by weight of the wettable powders is approximately 5% and that of the inert carrier material approximately 95% of the finished granules.

B. Biological examples

Example A (Prodenia litura)

Larvae of the Egyptian cotton worm (Prodenia litura, LIII) were sprayed together with cotton leaves with identical amounts of active substances, or mixtures thereof, in various concentrations. The larvae which had been treated in this manner were subsequently placed on the dried leaves. The effect of the active substances, or the active substance mixtures, were evaluated after 7 days at room temperature (21-23° C.).

| Active substance | Active substance ppm | Mortality in % |
|---|---|---|
| Compound Ia | 31 | 100 |
| | 16 | 100 |
| | 7.8 | 60 |
| | 3.9 | 0 |
| | 2.0 | 0 |
| | 1.0 | 0 |
| Compound XVa | 31 | 100 |
| | 16 | 100 |
| | 7.8 | 100 |
| | 3.9 | 40 |
| | 2.0 | 0 |
| | 1.0 | 6 |
| Ia + XVa | 31 + 31 | 100 |
| | 16 + 16 | 100 |
| | 7.8 + 7.8 | 100 |
| | 3.9 + 3.9 | 100 |
| | 2.0 + 2.0 | 50 |
| | 1.0 + 1.0 | 20 |
| Compound IX | 500 | 100 |
| | 250 | 60 |
| | 125 | 50 |
| | 63 | 30 |
| | 31 | 10 |
| Ia + IX | 31 + 500 | 100 |
| | 16 + 250 | 100 |
| | 7.8 + 125 | 100 |
| | 3.9 + 63 | 100 |
| | 2.0 + 32 | 40 |

-continued

| Active substance | Active substance ppm | Mortality in % |
|---|---|---|
| Deltamethrin (XIIIa) | 1.0 | 100 |
| | 0.98 | 90 |
| | 0.49 | 70 |
| | 0.24 | 0 |
| | 0.12 | 0 |
| Ia + deltamethrin (XIIIa) | 31 + 2.0 | 100 |
| | 16 + 0.98 | 100 |
| | 7.8 + 0.49 | 100 |
| | 3.9 + 0.24 | 90 |
| | 2.0 + 0.12 | 10 |

Example B (Tenebrio molitor)

Larvae of the meal beetle (Tenebrio molitor LIII) were sprayed uniformly together with starch wafers of 4 cm diameter with an identical amount of active substances, or mixtures thereof, in various concentrations. The larvae and wafers which had been treated in this manner were then placed in Petri dishes, and these were sealed and kept at room temperature (21-23° C.) for 7 days. The mortality (in %) was then determined.

| Active substance | Active substance ppm | Mortality in % |
|---|---|---|
| Compound Ia | 250 | 100 |
| | 125 | 100 |
| | 63 | 90 |
| | 31 | 70 |
| | 16 | 10 |
| Compound XVa | 125 | 80 |
| | 63 | 40 |
| | 31 | 10 |
| | 16 | 0 |
| | 8 | 0 |
| Ia + XVa | 250 + 125 | 100 |
| | 125 + 63 | 100 |
| | 63 + 31 | 100 |
| | 31 + 16 | 90 |
| | 16 + 8 | 40 |

Example C

Field beans (Vicia faba) which were heavily infested with cowpea aphids (Aphis craccivora) were sprayed with identical amounts of active substances, or mixtures thereof, in various concentrations.

The plants which were treated in this way were then placed in the greenhouse. The mortality of the aphids was determined after 3 days.

| Active substance | Active substance ppm | Mortality in % |
|---|---|---|
| Compound Ia | 63.0 | 40 |
| | 31.0 | 0 |
| | 16.0 | 0 |
| Compound IX | 7.8 | 20 |
| | 3.9 | 0 |
| | 2.0 | 0 |
| Ia + IX | 63.0 + 7.8 | 90 |
| | 31.0 + 3.9 | 80 |
| | 16.0 + 2.0 | 40 |
| Triazophos | 3.9 | 20 |
| | 2.0 | 0 |
| Ia + Triazophos | 31.0 + 3.9 | 60 |
| | 16.0 + 2.0 | 40 |
| Deltamethrin | 0.06 | 30 |
| | 0.03 | 15 |
| Ia + Deltamethrin | 7.8 + 0.06 | 85 |

| Active substance | Active substance ppm | Mortality in % |
|---|---|---|
| | 3.9 + 0.03 | 80 |

Example D

Bean plant (Phaseolus vulgaris) which were heavily infested with citrus mealybug (Pseudococcus citri) were sprayed with identical amounts of active substances, or mixtures thereof, in various concentrations. The test subjects were assessed after standing in the greenhouse for 7 days at 20–25° C.

| Active substance | Active substance ppm | Mortality in % |
|---|---|---|
| Compound Ia | 31.0 | 15 |
| | 16.0 | 0 |
| | 7.8 | 0 |
| Triazophos | 2.0 | 15 |
| | 0.98 | 0 |
| Ia + Triazophos | 16.0 + 2.0 | 60 |
| | 7.8 + 0.98 | 40 |
| Heptenophos | 7.8 | 0 |
| | 3.9 | 0 |
| Ia + Heptenophos | 31.0 + 7.8 | 75 |
| | 16.0 + 3.9 | 50 |

What is claimed is:

1. A pesticide containing at least one compound of formula I

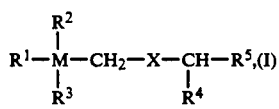

wherein:
M is carbon or silicon;
X is CH₂, O, S, NR⁶;
R¹ is (C₂–C₁₈) alkyl, (C₅–C₇) cycloalkyl, (C₂–C₈)alkenyl, phenyl, or naphthyl, all of which can be monosubstituted or polysubstituted;
R² and R³, independently of one another, are (C₁–C₃)alkyl, (C₂–C₈)alkenyl or phenyl, or R² and R³ are an alkylene chain which, together with the quaternary central atom M, form an unsubstituted or fluorinesubstituted ring having four to six ring members )when M=Si) or having three to six ring members (when M=C);
R⁴ is H, CN, CCl₃, C≡CH, (C₁–C₄alkyl, F or (C(=S)NH₂;
R⁵ is pyridyl, furyl or thienyl, each of which can be substituted, or is phthalimidyl, di(C₁–C₄)alkylmaleimidyl, thiophthalimidyl, dihydrophthalimidyl, tetrahydrophthalimidyl or substituted phenyl; or R⁴ and R⁵, together with the carbon atom linking them, form an indanyl, cyclopentenoyl or cyclopentenyl radical, each of which radicals can be substituted; and
R⁶ is H, (C₁–C₃)alkyl or phenyl;
in combination with a second compound selected from the group consisting of endosulan, deltamethrin, triazophos, heptenophos and ethyl N-[3,5-dichloro-4-(1,1,2,3,3,3-hexafluoropropoxy)phenyl)carbamoyl]-2-chlorobenzocarboximidate, wherein said compound of formula I and said second compound are combined in synergistically effective amounts.

2. A pesticide as claimed in claim 1, wherein said compound of formula I is (4-ethoxyphenyl)-(dimethyl)-silane.

3. A pesticide as claimed in claim 1, wherein said second compound is ethyl N-2-chlorobenzocarboximidate.

4. A pesticide as claimed in claim 1, containing (4-ethoxyphenyl)-(dimethyl)-silane in combination with ethyl N-2-chloro-benzocarboximidate.

5. A pesticide as claimed in claim 1, wherein the ratio by weight of the compound of formula I to said second compound is between 20:1 and 1:20.

6. A method of controlling insects, acarids or nematodes, which comprises treating an insect, acarid, nematode or an environment thereof with an effective amount of a pesticide as claimed in claim 8.

7. A pesticide as claimed in claim 1, wherein, in formula I,
X is CH₂ or oxygen;
R¹ is a group of formulae II to VIII

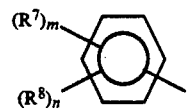

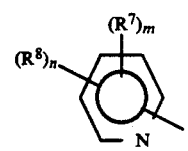

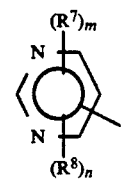

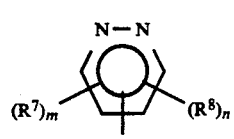

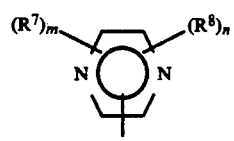

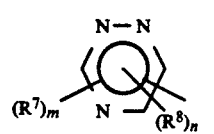

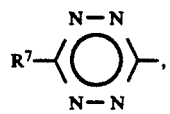

wherein
R⁷ and R⁸ independently of one another are H, (C₁–C₄)alkyl, tri (C₁–C₄)alkylsily, halogen, nitro, cyano, (C₂-C₆)alkenyl, (C₂-C₆)alkynyl, amino (C₃-C₇)cycloalkyl, phenyl, phenoxy, (C₁-C₅)alkoxy, (C₂-C₄)alkenyloxy, (C₂-C₄)-alkynyloxy, hydroxycarbonyl, (C₁-C₄)alkylthio, (C₃-C₇)cycloalkyloxy, (C₁-C₆)alkylcarbonyl, (C₁-C₄)alkoxycarbonyl, (C₂-C₄)alkenyloxycarbonyl, (C₃-C₅)alkynyloxycarbonyl, (C₁-C₄)haloalkyl, (C₁-C₄)alkoxy(C₁-C₄)alkyl, (C₁-C₃)haloalkoxy, (C₁-C₃)haloalkylthio, halo(C₁-C₄)alkoxy(C₁-C₄)alkyl, (C₁-C₄)alkylthio(C₁-C₄)alkyl, (C₁-C₄)alkoxy(C₁-C₄)alkoxy, halo(C₁-C₄)alkoxy(C₁-C₄)alkoxy, (C₂-C₄)alkenyloxy(C₁-C₄)alkoxy, halo(C₂-C₄)alkenyloxy, (C₁-C₄)alkoxy(C₁-C₄)alkylthio, (C₁-C₄)alkylthio(C₁-C₄)alkoxy, (C₁-C₄)alkythio(C₁-C₄)alkylthio, halo(C₁-C₄)alkoxycarbonyl, halo(C₂-C₄)alkenyloxycarbonyl or di(C₁-C₆alkyl)amino; or two radicals R⁷ or R⁸, when they are in the ortho position to each other, together are methylenedioxy, ethylenedioxy or a (C₃-C₅)alkylene radical; and m and n independently of one another are 0, 1 or 2;

R² and R³ are (C₁-C₃)alkyl or, together with the carbon atom linking them, are an unsubstituted or monofluorinated or difluorinated cyclopropyl ring when M=C;

R⁴ is hydrogen, fluorine, cyano or (C₁-C₄) alkyl;

R⁵ is a radical of formula A

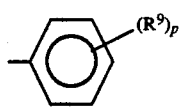

wherein the R⁹ substituents independently of one another are H, halogen, (C₁-C₄)alkyl, (C₁-C₄)alkoxy, (C₁-C₄)haloalkyl, phenyl or n-pyrrolyl, or R⁵ is a radical of formula B

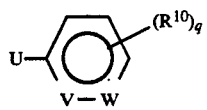

wherein the R¹⁰ substituents independently of one another are H, halogen, (C₁-C₄)alkyl, (C₁-C₄)alkoxy or (C₁-C₄)haloalkyl; U is CH₂; C=O, O or S; V and W are CH or N where W must be CH if V is N and vice versa; p is an integer from 1 to 5; and q is 1 or 2.

8. A pesticide as claimed in claim 7, wherein, in formula I, R⁷ and R⁸ are hydrogen, halogen, (C₁-C₄)alkyl, (C₂-C₆)alkenyl, (C₃-C₇)cycloalkyl, (C₁-C₅)alkoxy, (C₂-C₄)alkenyloxy, (C₁-C₄)alkylthio, (C₁-C₄)haloalkyl or (C₁-C₃)haloalkoxy, or R⁷ or R⁸ together are methylenedioxy and are orientated in the 3- or 4-position of a six member aromatic ring.

9. A pesticide as claimed in claim 7, wherein, in formula I, R² and R³ are methyl, ethyl, isopropyl or n-propyl; R⁴ is hydrogen; U is oxygen; and when R⁹ is fluorine, p is 5, or when R⁹ is a radical of formula B, p is 1 or 2.

10. A pesticide as claimed in claim 7, wherein in formula I, R⁵ is a radical of formula A wherein R⁹ is H or 4-fluorine, or R⁵ is a radical of formula B which is oriented relative to A in the 3-position of the phenyl radical.

11. A pesticide as claimed in claim 7, wherein, in formula I, R⁵ is a monosubstituted or disubstituted pyridyl group of formula C

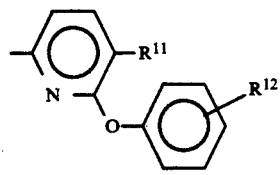

wherein R¹¹ is halogen or hydrogen and R¹² is hydrogen, F, Cl, Br, (C₁-C₄)alkyl, (C₁-C₄)alkoxy or (C₁-C₄)haloalkyl, 12. A pesticide as claimed in claim 7, wherein, in formula I, R⁵ is a heterocycle of formula D

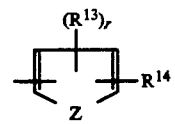

wherein Z is O or S R¹³ is H, halogen, (C₁-C₄)alkyl, (C₁-C₄)alkoxy, (C₁-C₄)haloalkyl, CN or NO₂; R¹⁴ is benzyl, propargyl, allyl or phenoxy all of which can be substituted; and r is 1 or 2.

13. A pesticide as claimed in claim 7, containing (4-ethoxyphenyl)-(dimethyl)-silane in combination with endosulfan.

14. A pesticide as claimed in claim 7, containing (4-ethoxyphenyl)-(dimethyl)-silane in combination with deltamethrin.

15. A pesticide a claimed in claim 7, containing (4-ethoxyphenyl)-(dimethyl)-silane in combination with triazophos.

16. A pesticide as claimed in claim 7, containing (4-ethoxyphenyl)-(dimethyl)-silane in combination with heptenophos.

17. A pesticide containing (4-ethoxyphenyl)-(dimethyl)-silane in combination with endosulfan, wherein the ratio by weight of said first compound to said second compound is between 1:15.6 and 1:16.15.

18. A pesticide containing (4-ethoxyphenyl)-(dimethyl)-silane in combination with deltamethrin, wherein the ratio by weight of said first compound to said second compound is between 16.6:1 and 15.5:1.

19. A pesticide containing (4-ethoxyphenyl)-(dimethyl)-silane in combination with triazophos, wherein the ratio by weight of said first compound to said second is between 7.9:1 and 8:1.

20. A pesticide containing (4-ethoxyphenyl)-(dimethyl)-silane in combination with ethyl N-2-chloro-benzocarboximidate, wherein the ratio by weight of said first compound to said second compound is between 1:1 and 2:1.

21. A method of controlling insects, acarids or nematodes, which comprises treating an insect, acarid, nematode or an environment thereof with an effective amount of a pesticide as claimed in claim 17.

22. A method of controlling insects, acarids or nematodes, which comprises treating an insect, acarid, nematode or an environment thereof with an effective amount of a pesticide as claimed in claim 18.

23. A method of controlling insects, acarids or nematodes, which comprises treating an insect, acarid, nematode or an environment thereof with an effective amount of a pesticide as claimed in claim 19.

24. A method of controlling insects, acarids or nematodes, which comprises treating an insect, acarid, nematode or an environment thereof with an effective amount of a pesticide as claimed in claim 20.

* * * * *